(12) United States Patent
Seiger et al.

(10) Patent No.: US 9,775,588 B2
(45) Date of Patent: *Oct. 3, 2017

(54) BIOPSY DEVICE

(71) Applicant: C. R. Bard, Inc., Tempe, AZ (US)

(72) Inventors: Jason Seiger, Gilbert, AZ (US); Rafal Chudzik, Peoria, AZ (US); Angela Jensen, Mesa, AZ (US); Glen Lazok, Mesa, AZ (US)

(73) Assignee: C. R. Bard, Inc., Tempe, AZ (US)

( * ) Notice: Subject to any disclaimer, the term of this patent is extended or adjusted under 35 U.S.C. 154(b) by 469 days.

This patent is subject to a terminal disclaimer.

(21) Appl. No.: 14/502,445

(22) Filed: Sep. 30, 2014

(65) Prior Publication Data
US 2015/0018712 A1    Jan. 15, 2015

Related U.S. Application Data

(60) Continuation of application No. 14/074,051, filed on Nov. 7, 2013, now Pat. No. 8,858,463, which is a
(Continued)

(51) Int. Cl.
  *A61B 10/02* (2006.01)
  *A61M 1/00* (2006.01)
  *A61M 5/31* (2006.01)

(52) U.S. Cl.
  CPC ...... *A61B 10/0283* (2013.01); *A61B 10/0275* (2013.01); *A61B 2217/005* (2013.01); *A61M 1/0056* (2013.01); *A61M 2005/3123* (2013.01)

(58) Field of Classification Search
  CPC . A61M 1/0009; A61M 1/0037; A61M 1/0039
(Continued)

(56) References Cited

U.S. PATENT DOCUMENTS 737,293 A    8/1903    Summerfeldt
1,585,934 A    5/1926    Muir
(Continued)

FOREIGN PATENT DOCUMENTS

CN    101011268 A    8/2007
CN    101032420 A    9/2007
(Continued)

OTHER PUBLICATIONS

Maxim; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; pp. 1-14; Rev 1.
(Continued)

*Primary Examiner* — Michael C Stout

(57) ABSTRACT

A biopsy device includes a pressure chamber having a body having a distal end and a proximal end, wherein the proximal end includes an inlet. At least one first recessed area extends along an inner wall of the body, proximate the proximal end of the body of the pressure chamber. The first recessed area is configured to release pressure within the pressure chamber. At least one second recessed area extends along the inner wall of the body, proximate the distal end of the body of the pressure chamber. The second recessed area is configured to release pressure within the pressure chamber. A cannula is coupled to the pressure chamber for taking a tissue sample from a patient. The cannula defines a tissue chamber. A fluid receptacle is interposed between the tissue chamber and the pressure chamber. The fluid receptacle has an absorbent material to absorb a fluid.

12 Claims, 2 Drawing Sheets

Related U.S. Application Data division of application No. 13/550,895, filed on Jul. 17, 2012, now Pat. No. 8,597,205, which is a division of application No. 11/961,909, filed on Dec. 20, 2007, now Pat. No. 8,241,225.

(58) Field of Classification Search
USPC .................................................. 600/562–567
See application file for complete search history.

(56) References Cited

U.S. PATENT DOCUMENTS

| | | | |
|---|---|---|---|
| 1,663,761 A | 3/1928 | Johnson | |
| 2,953,934 A | 9/1960 | Sundt | |
| 3,019,733 A | 2/1962 | Braid | |
| 3,224,434 A * | 12/1965 | Molomut | A61B 10/02 433/91 |
| 3,289,669 A | 12/1966 | Dwyer et al. | |
| 3,477,423 A | 11/1969 | Griffith | |
| 3,512,519 A | 5/1970 | Hall | |
| 3,561,429 A | 2/1971 | Jewett et al. | |
| 3,565,074 A | 2/1971 | Foti | |
| 3,606,878 A | 9/1971 | Kellogg | |
| 3,727,602 A | 4/1973 | Hyden et al. | |
| 3,732,858 A | 5/1973 | Banko | |
| 3,785,380 A | 1/1974 | Brumfield | |
| 3,800,783 A | 4/1974 | Jamshidi | |
| 3,844,272 A | 10/1974 | Banko | |
| 3,882,849 A | 5/1975 | Jamshidi | |
| 3,889,682 A | 6/1975 | Denis et al. | |
| 3,916,948 A | 11/1975 | Benjamin | |
| 4,275,730 A * | 6/1981 | Hussein | A61M 5/488 604/121 |
| 4,282,884 A | 8/1981 | Boebel | |
| 4,306,570 A | 12/1981 | Matthews | |
| 4,354,092 A | 10/1982 | Manabe et al. | |
| 4,393,879 A | 7/1983 | Milgrom | |
| 4,445,509 A | 5/1984 | Auth | |
| 4,490,137 A | 12/1984 | Moukheibir | |
| 4,549,554 A | 10/1985 | Markham | |
| 4,577,629 A | 3/1986 | Martinez | |
| 4,589,414 A | 5/1986 | Yoshida et al. | |
| 4,603,694 A | 8/1986 | Wheeler | |
| 4,605,011 A | 8/1986 | Naslund | |
| 4,616,215 A | 10/1986 | Maddalena | |
| 4,617,430 A | 10/1986 | Bryant | |
| 4,620,539 A | 11/1986 | Andrews et al. | |
| 4,643,197 A | 2/1987 | Greene et al. | |
| 4,645,153 A | 2/1987 | Granzow et al. | |
| 4,678,459 A | 7/1987 | Onik et al. | |
| 4,696,298 A | 9/1987 | Higgins et al. | |
| 4,702,260 A | 10/1987 | Wang | |
| 4,706,687 A | 11/1987 | Rogers | |
| 4,776,346 A | 10/1988 | Beraha et al. | |
| 4,792,327 A | 12/1988 | Swartz | |
| 4,832,044 A | 5/1989 | Garg | |
| 4,844,064 A | 7/1989 | Thimsen et al. | |
| 4,844,087 A | 7/1989 | Garg | |
| 4,850,354 A | 7/1989 | McGurk-Burleson et al. | |
| 4,893,635 A | 1/1990 | de Groot et al. | |
| 4,907,598 A | 3/1990 | Bauer | |
| RE33,258 E | 7/1990 | Onik et al. | |
| 4,940,061 A | 7/1990 | Terwilliger et al. | |
| 4,952,817 A | 8/1990 | Bolan et al. | |
| 4,958,625 A | 9/1990 | Bates et al. | |
| 4,967,762 A | 11/1990 | DeVries | |
| 4,986,278 A | 1/1991 | Ravid et al. | |
| 4,986,279 A | 1/1991 | O'Neill | |
| 4,986,807 A | 1/1991 | Farr | |
| 4,989,614 A | 2/1991 | Dejter, Jr. et al. | |
| 5,025,797 A | 6/1991 | Baran | |
| 5,048,538 A | 9/1991 | Terwilliger et al. | |
| 5,057,822 A | 10/1991 | Hoffman | |
| 5,078,603 A | 1/1992 | Cohen | |
| 5,125,413 A | 6/1992 | Baran | |
| 5,138,245 A | 8/1992 | Mattinger et al. | |
| 5,146,921 A | 9/1992 | Terwilliger et al. | |
| 5,156,160 A | 10/1992 | Bennett | |
| 5,158,528 A | 10/1992 | Walker et al. | |
| 5,172,702 A | 12/1992 | Leigh et al. | |
| 5,176,628 A | 1/1993 | Charles et al. | |
| 5,183,052 A | 2/1993 | Terwilliger | |
| 5,197,484 A | 3/1993 | Kornberg et al. | |
| 5,211,627 A | 5/1993 | William | |
| 5,223,012 A | 6/1993 | Best et al. | |
| 5,225,763 A | 7/1993 | Krohn et al. | |
| 5,234,000 A | 8/1993 | Hakky et al. | |
| 5,236,334 A | 8/1993 | Bennett | |
| 5,242,404 A | 9/1993 | Conley et al. | |
| 5,249,583 A | 10/1993 | Mallaby | |
| 5,282,476 A | 2/1994 | Terwilliger | |
| 5,282,477 A | 2/1994 | Bauer | |
| 5,290,253 A | 3/1994 | Kira | |
| 5,324,306 A | 6/1994 | Makower et al. | |
| 5,334,183 A | 8/1994 | Wuchinich | |
| 5,335,671 A | 8/1994 | Clement | |
| 5,368,029 A | 11/1994 | Holcombe et al. | |
| 5,368,045 A | 11/1994 | Clement et al. | |
| 5,383,874 A | 1/1995 | Jackson et al. | |
| 5,397,462 A | 3/1995 | Higashijima et al. | |
| 5,400,798 A | 3/1995 | Baran | |
| 5,439,474 A | 8/1995 | Li | |
| 5,458,112 A | 10/1995 | Weaver | |
| 5,469,860 A | 11/1995 | De Santis | |
| 5,471,994 A | 12/1995 | Guirguis | |
| 5,479,486 A | 12/1995 | Saji | |
| 5,485,917 A | 1/1996 | Early | |
| 5,492,130 A | 2/1996 | Chiou | |
| 5,511,556 A | 4/1996 | DeSantis | |
| 5,526,822 A | 6/1996 | Burbank et al. | |
| 5,535,755 A | 7/1996 | Heske | |
| 5,546,957 A | 8/1996 | Heske | |
| 5,554,151 A | 9/1996 | Hinchliffe | |
| 5,560,373 A | 10/1996 | De Santis | |
| 5,564,436 A | 10/1996 | Hakky et al. | |
| 5,569,284 A | 10/1996 | Young et al. | |
| 5,575,293 A | 11/1996 | Miller et al. | |
| 5,591,170 A | 1/1997 | Spievack et al. | |
| 5,601,583 A | 2/1997 | Donahue et al. | |
| 5,601,585 A | 2/1997 | Banik et al. | |
| 5,602,449 A | 2/1997 | Krause et al. | |
| 5,612,738 A | 3/1997 | Kim | |
| 5,617,874 A | 4/1997 | Baran | |
| 5,649,547 A | 7/1997 | Ritchart et al. | |
| 5,655,542 A | 8/1997 | Weilandt | |
| 5,655,657 A | 8/1997 | Roshdy | |
| 5,665,101 A | 9/1997 | Becker et al. | |
| 5,669,394 A | 9/1997 | Bergey et al. | |
| 5,699,909 A | 12/1997 | Foster | |
| 5,700,265 A | 12/1997 | Romano | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A | 5/1998 | Murphy-Chutorian | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,779,649 A | 7/1998 | Herbert | |
| 5,788,651 A | 8/1998 | Weilandt | |
| 5,792,167 A | 8/1998 | Kablik et al. | |
| 5,807,282 A | 9/1998 | Fowler | |
| 5,817,033 A * | 10/1998 | DeSantis | A61B 10/0275 600/562 |
| 5,817,034 A | 10/1998 | Milliman et al. | |
| 5,823,970 A | 10/1998 | Terwilliger | |
| 5,827,305 A | 10/1998 | Gordon | |
| 5,830,219 A | 11/1998 | Bird et al. | |
| D403,405 S | 12/1998 | Terwilliger | |
| 5,857,982 A | 1/1999 | Milliman et al. | |
| 5,871,699 A | 2/1999 | Ruggeri | |
| 5,879,365 A | 3/1999 | Whitfield et al. | |
| 5,908,233 A | 6/1999 | Heskett et al. | |
| 5,913,857 A | 6/1999 | Ritchart et al. | |

(56) References Cited

U.S. PATENT DOCUMENTS

| | | |
|---|---|---|
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,032,673 A | 3/2000 | Savage et al. |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 * | 11/2008 | Rassman ............ A61B 17/3468 600/566 |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |

(56) References Cited

U.S. PATENT DOCUMENTS

| | | |
|---|---|---|
| 7,828,747 B2 | 11/2010 | Heske et al. |
| 7,841,991 B2 | 11/2010 | Douglas et al. |
| 7,846,109 B2 | 12/2010 | Parihar |
| 7,862,517 B2 | 1/2011 | Tsonton et al. |
| 7,862,518 B2 | 1/2011 | Parihar |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,959,580 B2 | 6/2011 | Mccullough et al. |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,073,008 B2 | 12/2011 | Mehta et al. |
| 8,083,671 B2 | 12/2011 | Boulais et al. |
| 8,109,885 B2 | 2/2012 | Heske et al. |
| 8,118,755 B2 | 2/2012 | Hibner et al. |
| 8,152,738 B2 | 4/2012 | Li et al. |
| 8,157,744 B2 | 4/2012 | Jor Rgensen et al. |
| 8,162,851 B2 | 4/2012 | Heske et al. |
| 8,172,773 B2 | 5/2012 | Heske et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,916 B2 | 8/2012 | Speeg et al. |
| 8,251,917 B2 | 8/2012 | Almazan |
| 8,262,585 B2 | 9/2012 | Thompson et al. |
| 8,262,586 B2 | 9/2012 | Anderson et al. |
| 8,267,868 B2 | 9/2012 | Taylor et al. |
| 8,277,393 B2 | 10/2012 | Miller et al. |
| 8,282,574 B2 | 10/2012 | Coonahan et al. |
| 8,283,890 B2 | 10/2012 | Videbaek |
| 8,313,444 B2 | 11/2012 | Thompson et al. |
| 8,343,069 B2 | 1/2013 | Uchiyama et al. |
| 8,366,636 B2 | 2/2013 | Videbaek |
| 8,430,824 B2 | 4/2013 | Videbaek et al. |
| 8,430,827 B2 | 4/2013 | Nicoson et al. |
| 8,485,987 B2 | 7/2013 | Videbaek et al. |
| 8,485,989 B2 | 7/2013 | Videbaek |
| 8,597,206 B2 | 12/2013 | Videback |
| 8,702,621 B2 | 4/2014 | Mccullough et al. |
| 8,702,622 B2 | 4/2014 | McCullough et al. |
| 8,728,004 B2 | 5/2014 | Heske et al. |
| 8,771,200 B2 | 7/2014 | Thompson et al. |
| 8,956,306 B2 | 2/2015 | Hibner |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1* | 1/2002 | Tanaka ............... A61M 1/3633 210/263 |
| 2002/0029007 A1 | 3/2002 | Bryan et al. |
| 2002/0067151 A1 | 6/2002 | Tanishita |
| 2002/0068878 A1 | 6/2002 | Jasonni et al. |
| 2002/0082518 A1* | 6/2002 | Weiss ............... A61B 10/0283 600/566 |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1 | 10/2002 | Neuenfeldt |
| 2002/0151822 A1 | 10/2002 | Burdorff et al. |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0073929 A1 | 4/2003 | Baltschun et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0165329 A1 | 7/2005 | Taylor et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Selis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0074350 A1 | 4/2006 | Cash |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0173377 A1* | 8/2006 | McCullough ...... A61B 10/0275 600/566 |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0123797 A1 | 5/2007 | Krause |
| 2007/0149893 A1 | 6/2007 | Heske et al. |
| 2007/0149895 A1 | 6/2007 | McCullough et al. |
| 2007/0161925 A1 | 7/2007 | Quick et al. |

(56) References Cited

U.S. PATENT DOCUMENTS

| | | |
|---|---|---|
| 2007/0167736 A1 | 7/2007 | Dietz et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1* | 11/2007 | Frass ................ A61B 10/0045 600/567 |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1 | 5/2008 | Ryan et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0015208 A1 | 1/2009 | White et al. |
| 2009/0030405 A1 | 1/2009 | Quick et al. |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Arnin |
| 2009/0137927 A1 | 5/2009 | Miller |
| 2009/0146609 A1 | 6/2009 | Santos |
| 2009/0171243 A1 | 7/2009 | Hibner et al. |
| 2009/0204022 A1 | 8/2009 | Schwindt |
| 2009/0227893 A1 | 9/2009 | Coonahan et al. |
| 2009/0281453 A1 | 11/2009 | Tsonton et al. |
| 2010/0030020 A1 | 2/2010 | Sanders et al. |
| 2010/0030108 A1 | 2/2010 | Anderson et al. |
| 2010/0063416 A1 | 3/2010 | Cicenas et al. |
| 2010/0106053 A1 | 4/2010 | Videbaek et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0222700 A1 | 9/2010 | Hibner |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2010/0324449 A1 | 12/2010 | Rostaing et al. |
| 2011/0021946 A1 | 1/2011 | Heske et al. |
| 2011/0054350 A1 | 3/2011 | Videbaek |
| 2011/0077551 A1 | 3/2011 | Videbaek |
| 2011/0087131 A1 | 4/2011 | Videbaek |
| 2011/0105945 A1 | 5/2011 | Videbaek et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0208085 A1 | 8/2011 | Mccullough et al. |
| 2011/0295150 A1 | 12/2011 | Mccullough et al. |
| 2012/0071787 A1 | 3/2012 | Reuber et al. |
| 2012/0095366 A1 | 4/2012 | Heske et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0238905 A1 | 9/2012 | Heske et al. |
| 2012/0310109 A1 | 12/2012 | Almazan |
| 2012/0323120 A1 | 12/2012 | Taylor et al. |
| 2012/0323140 A1 | 12/2012 | Taylor et al. |
| 2012/0330185 A1 | 12/2012 | Coonahan et al. |
| 2013/0023789 A1 | 1/2013 | Anderson et al. |
| 2013/0023791 A1 | 1/2013 | Thompson et al. |
| 2013/0289441 A1 | 10/2013 | Videbaek et al. |
| 2014/0228706 A1 | 8/2014 | Mccullough et al. |
| 2014/0371585 A1 | 12/2014 | Thompson et al. |
| 2015/0025415 A1 | 1/2015 | Videbaek et al. |
| 2015/0073301 A1 | 3/2015 | Videbaek et al. |
| 2015/0094613 A1 | 4/2015 | Jorgensen et al. |
| 2015/0133814 A1 | 5/2015 | Almazan |
| 2015/0148702 A1 | 5/2015 | Heske et al. |
| 2015/0190124 A1 | 7/2015 | Mccullough et al. |
| 2015/0238174 A1 | 8/2015 | Reuber et al. |
| 2015/0342579 A1 | 12/2015 | Heske et al. |
| 2016/0256138 A1 | 9/2016 | Videbaek et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1698282 A1 | 9/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| GB | 2323288 A | 9/1998 |
| JP | 1-126957 A | 9/1987 |
| JP | H10508504 A | 8/1998 |

(56) References Cited

FOREIGN PATENT DOCUMENTS

| | | |
|---|---|---|
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9734531 A1 | 9/1997 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |
| WO | 2008131362 A2 | 10/2008 |
| WO | 2010107424 A1 | 9/2010 |
| WO | 2010120294 A1 | 10/2010 |
| WO | 2011019343 A1 | 2/2011 |
| WO | 2013158072 A1 | 10/2013 |

OTHER PUBLICATIONS

Merriam-Webster.com, Within—Definition and More from the Free Merriam-Webster Dictionary, downloaded Aug. 15, 2014, 3 pages.
Merriam-Webster.com, Series—Definition and More from the Free Merriam-Webster Dictionary, downloaded Aug. 15, 2014, 3 pages.
Merriam-Webster.com, Restrain—Definition and More from the Free Merriam-Webster Dictionary, downloaded Aug. 17, 2014, 3 pages.
Merriam-Webster.com, While—Definition and More from the Free Merriam-Webster Dictionary, downloaded Aug. 17, 2014, 4 pages.

* cited by examiner

BIOPSY DEVICE

CROSS-REFERENCE TO RELATED APPLICATIONS

This is a continuation of U.S. patent application Ser. No. 14/074,051, filed Nov. 7, 2013, now U.S. Pat. No. 8,858,463, which is a division of U.S. patent application Ser. No. 13/550,895, filed Jul. 17, 2012, now U.S. Pat. No. 8,597,205, which is a division of U.S. patent application Ser. No. 11/961,909, filed Dec. 20, 2007, now U.S. Pat. No. 8,241,225, each of which is incorporated herein by reference.

FIELD OF THE DISCLOSURE

The present disclosure relates generally to a biopsy device. More specifically, the present disclosure relates to a biopsy device and a method for extracting a tissue sample therein.

BACKGROUND

In medical procedures, various biopsy devices are used for taking tissue samples. Typically, a biopsy device includes a hand piece with a hollow biopsy cannula/needle, a sampling chamber, a sample separating mechanism, and a pressure generator. A portion of the hollow biopsy cannula/needle protrudes from the hand piece and is introduced into the tissue being investigated. A sample of the tissue is sucked into the sampling chamber by vacuum, separated by the sample separating mechanism, and then removed. The pressure generator, such as a pressure chamber with a single piston, generates the vacuum.

Unfortunately, large amounts of pressure can build-up within the pressure chamber of the biopsy device. The pressure build-up can decrease the efficiency and reliability of tissue extraction from the sampling chamber. Accordingly, there is the need for a biopsy device that prevents pressure build-up and provides reliable tissue extraction.

DETAILED DESCRIPTION OF THE DRAWINGS

Figure 1:
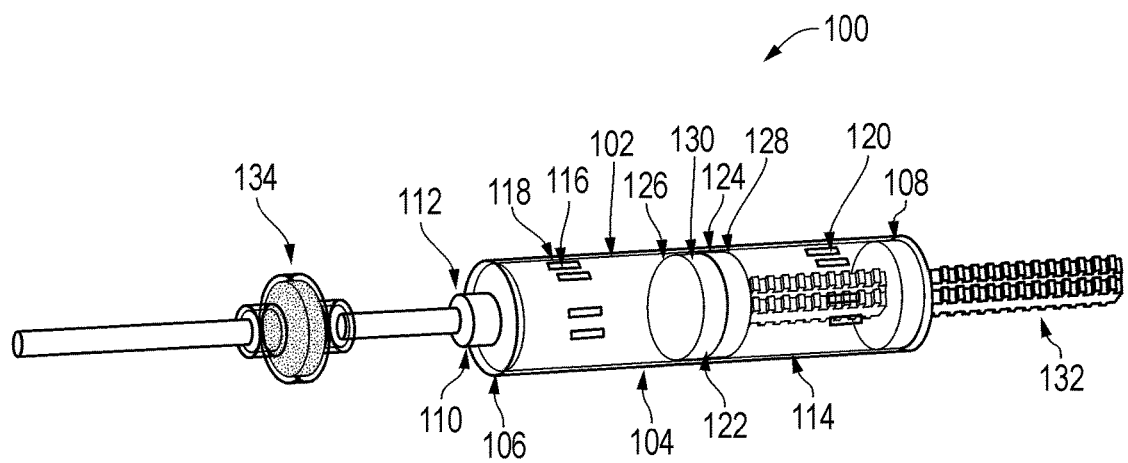
FIG. 1 is a side view of a first embodiment of a biopsy device.

A biopsy device is disclosed. The biopsy device includes a chamber having a body having a distal end and a proximal end, wherein the proximal end includes an inlet. The biopsy device further includes a vacuum generator for generating negative and positive pressure and at least one first recessed area and at least one second recessed area. The first recessed area extends along an inner wall of the body, proximate the proximal end of the body of the chamber. The first recessed area is configured to release pressure within the chamber. The second recessed area extends along the inner wall of the body, proximate the distal end of the body of the chamber. The second recessed area is configured to release pressure within the chamber. The biopsy device further includes a cannula coupled to the chamber for taking a tissue sample from a patient.

In another embodiment, a biopsy device is provided. The biopsy device includes a chamber having a body having a distal end, a proximal end, and an inner wall. The proximal end includes an inlet. The biopsy device further includes at least one first recessed area and at least one second recessed area. The first recessed area extends along the inner wall of the body, proximate the proximal end of the body of the chamber and is configured to release pressure within the chamber. The second recessed area extends along the inner wall of the body, proximate the distal end of the body of the chamber and is configured to release pressure within the chamber. The biopsy device further includes a piston configured to engage the inner wall of the chamber and a cannula coupled to the chamber for taking a tissue sample from a patient.

In a further embodiment, a biopsy device is provided. The biopsy device includes a cannula having a body having a distal end, a proximal end. An orifice is located on a circumferential surface of the proximal end of the cannula and is configured to receive a tissue sample into a lumen of said cannula. A pressure chamber is coupled to the distal end of the cannula. The pressure chamber has a body having a proximal end and a distal end. At least one first recessed area extends along an inner wall of the body, proximate the proximal end of the body of the pressure chamber. The first recessed area is configured to release pressure within the cannula. At least one second recessed area extends along the inner wall of the body, proximate the distal end of the body of the pressure chamber. The second recessed area is configured to release pressure within the cannula. Further included is a pressure generator for generating a pressure in the pressure chamber and altering a pressure in the lumen of the cannula. The biopsy device further includes a cutting sheath slidably and coaxially disposed over the cannula. The sheath is adapted to seal the recessed area of the orifice.

In yet another embodiment, a method of extracting a tissue sample from a biopsy device is disclosed. The method includes inserting a needle into a patient's body, wherein the needle is fluidly connected to a chamber. The chamber has a body having a distal end, a proximal end, at least one first recessed area, and at least one second recessed area. The first recessed area extends along an inner wall of the body, proximate the proximal end of the body of the chamber and is configured to release pressure within the chamber. The second recessed area extends along the inner wall of the body, proximate the distal end of the body of the chamber and is configured to release pressure within the chamber. The method further includes generating a negative pressure environment in the chamber relative to an atmospheric pressure surrounding the chamber and removing the tissue sample from the patient's body through a suction resulting from the negative pressure environment. The tissue sample is received into a proximal inlet of the cannula. The method includes removing the cannula from the patient's body, generating a positive pressure environment in the chamber relative to an atmospheric pressure surrounding the chamber, releasing the positive pressure environment through the first recessed area on the cylindrical body, and removing the tissue sample from the cannula.

Description of a First Embodiment of a Biopsy Device

Referring initially to FIG. 1, a first embodiment of a biopsy device is disclosed and is generally designated 100. The biopsy device includes a chamber 102 having a body 104 with a proximal end 106 and a distal end 108. The proximal end 106 of the chamber 102 can include an inlet 110. In an embodiment, the inlet 110 is configured to provide a fluid connection between a cannula (not shown) and the chamber 102. The cannula may include any configuration for severing a tissue sample from a patient. For instance, the cannula may include a knife or a cutting sheath to sever the tissue sample. In an example, the inlet 110 can include a needle hilt 112.

Figure 1A:
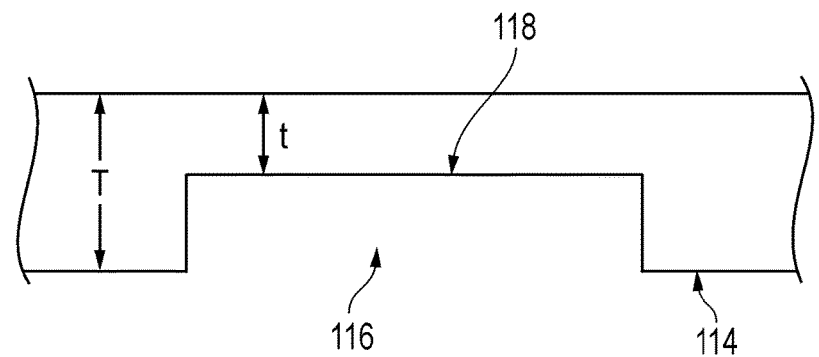
FIG. 1A is a side view of a magnified portion of a biopsy device.

The chamber 102 includes an inner wall 114. Located near the proximal end 106 of the chamber 102 is at least one first recessed area 116. As seen in FIG. 1A, the wall portion 118 of the recessed area 116 has a thickness "t" that is less than the thickness "T" of the inner wall 114. "At least one" first recessed area 116 as used herein includes one or more recessed area that extends along the inner wall 114 of the proximal end 106 of the chamber 102. The at least one first recessed area 116 is configured to release pressure within the chamber 102. The first recessed area 116 is illustrated as having a longitudinal shape. "Longitudinal shape" as used herein refers to an opening having an aspect ratio (length to width) greater than about 1.5:1, such as 2:1 and greater, and is oriented such that the long axis of the opening is generally parallel with the longitudinal axis of the chamber. Alternatively, the first opening 116 can have any cross-section that can be engaged to release pressure within the chamber 102 such as square, rectangular, diagonal, latitudinal, circular, any polygonal shape, or a combination thereof. "Latitudinal" and "diagonal" shapes are elongate as described above with respect to longitudinal shapes, but are positioned (i) generally perpendicular and (ii) generally non-perpendicular and non parallel to the longitudinal axis of the chamber. Further included along the inner wall 114 of the chamber 102 is at least one second recessed area 120 configured to release pressure within the chamber 102. "At least one" second recessed area 120 as used herein includes one or more recessed area that extends along the inner wall 114 of the distal end 108 of the chamber 102. The second recessed area 120 is illustrated as having a longitudinal shape. Alternatively, the second recessed area 120 can have any cross-section that can be engaged to release pressure within the chamber 102 such as square, rectangular, diagonal, latitudinal, circular, any polygonal shape, or a combination thereof.

The chamber 102 includes a pressure generating device. In an embodiment and as shown in FIG. 1, the pressure generating device may be a piston 122 disposed within the chamber 102. The piston 122 is dimensioned to engage the inner wall 114 of the chamber 102. Typically, the piston 122 may be of any configuration to engage the inner wall 114 of the chamber 102 in a substantially airtight fit. In an example, the piston 122 may be cylindrical in shape and have an outside diameter. Further, the inner wall 114 of the chamber 102 may be cylindrical in shape wherein the outside diameter of the piston 122 is more than the diameter of the inner wall 114 to form a substantially airtight fit. "Substantially airtight fit" as used herein refers to a frictional fit of the inner wall 114 and the piston 122 to prevent any air from escaping the chamber 102 through the distal end 108 of the chamber 102. In an embodiment, the piston 122 and chamber 102 may be of any suitable configuration to provide a substantially airtight fit.

As seen in FIG. 1, the piston 122 can include a body 124 having a proximal end 126 and a distal end 128. The proximal end 126 can include a piston seal 130. The piston seal 130 may be configured to provide the substantially airtight fit between the inner wall 114 and the piston 122. The distal end 128 of the piston 122 can include a stem 132. The stem 132 is configured to move the piston 122 within the chamber 102. The stem 132 may be incorporated into, or integrally formed with the distal end 128 of the piston 122. In an exemplary embodiment, as the piston 122 is depressed, the piston 122 moves toward the proximal end 106 of the chamber 102. The stem 132 as illustrated is a bar having a threaded cross-section. Alternatively, the stem 132 can have any cross-section that can be engaged for movement such as square, rectangular, any polygonal shape, or a combination thereof.

In a particular embodiment, the stem 132 is depressed and the piston 122 advances into the chamber 102 of the biopsy device 100. In particular, depressing the piston 122 toward the proximal end 106 of the chamber 102 but distal to the first recessed area 116 generates a positive pressure within the chamber 102, relative to an atmospheric pressure. Further depressing the piston 122 to engage the first recessed area 116 releases the positive pressure within the chamber 102. In an embodiment, the positive pressure is normalized to atmospheric pressure. In a further embodiment, advancing the piston 122 toward to distal end 108 of the chamber 102 but proximal to the second recessed area 120 generates a negative pressure within the chamber 102, relative to an atmospheric pressure. Further advancing the piston 122 to engage the second recessed area 120 releases the negative pressure within the chamber 102. In an embodiment, the negative pressure is normalized to atmospheric pressure.

In a further embodiment, generating a negative pressure within the chamber 102 provides pressure capable of removing a tissue sample from a biopsy cavity. The negative pressure provides a suction of the tissue sample from the biopsy cavity. The second recessed area 120 releases the negative pressure to prevent an excess build-up of pressure. Generating a positive pressure within the chamber 102 provides pressure capable of removing the tissue sample from the biopsy device 100. The first recessed area 116 releases the positive pressure to prevent an excess build-up of pressure, resulting in a safe sample ejection.

In an embodiment, the chamber 102 may include a fluid receptacle 134. The fluid receptacle 134 may be located at the proximal end 106 of the chamber 102. The fluid receptacle 134 is configured to absorb any excess fluid that is received within the chamber 102 during tissue sample removal. The fluid receptacle 134 traps the fluid so the fluids are contained within the fluid receptacle 134. In an embodiment, the fluid receptacle 134 may be of any suitable configuration to absorb any blood or tissue as well as allow air to pass through the fluid receptacle 134. In an embodiment, the fluid receptacle 134 may be an absorbent material capable of absorbing fluid. An exemplary absorbent material is fabric such as cotton, cellulose, and polyvinyl alcohol (PVA).

Description of a Second Embodiment of a Biopsy Device

Figure 2:
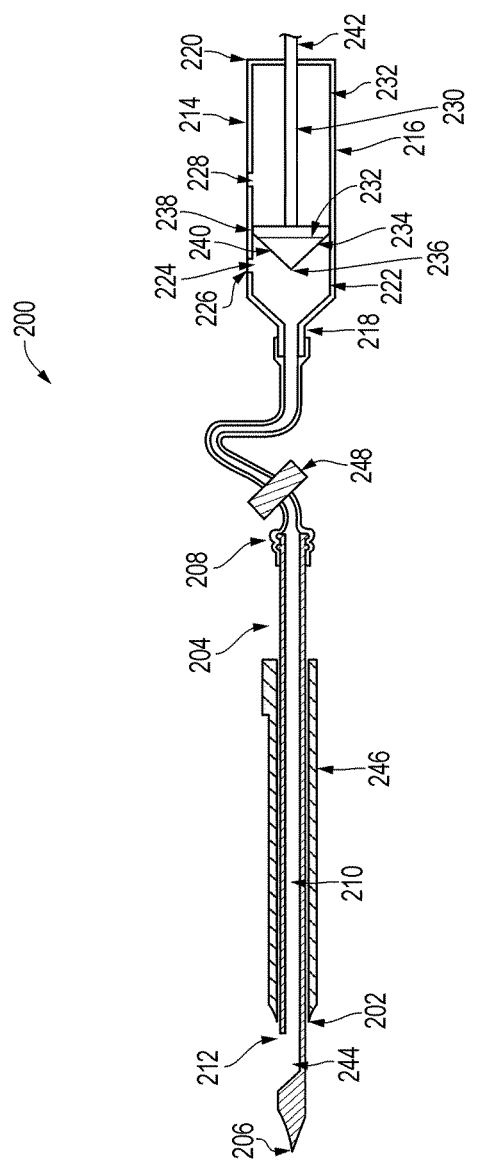
FIG. 2 is a side view of a second embodiment of a biopsy device.

Referring initially to FIG. 2, a second embodiment of a biopsy device is disclosed and is generally designated 200. The biopsy device includes a cannula 202. The cannula 202 has a body 204 having a proximal end 206 that forms a cutting or piercing leading edge, a distal end 208, and a lumen 210 therethrough. The proximal end 206 of the cannula 202 can include an orifice 212. The orifice 212 is configured to receive a tissue sample. The distal end 208 of the cannula 202 can include a pressure chamber 214 having a body 216 with a proximal end 218 and a distal end 220. The pressure chamber 214 includes an inner wall 222. Located near the proximal end 218 of the pressure chamber 214 is at least one first recessed area 224. The wall portion 226 of the recessed area 224 has a thickness that is less than the thickness of the inner wall 222. "At least one" first recessed area 224 as used herein includes one or more recessed area that extends along the inner wall 222 of the proximal end 218 of the pressure chamber 214. The at least one first recessed area 224 is configured to release pressure within the chamber 214 and the lumen 210 of the cannula 202. The first recessed area 224 is illustrated as having a longitudinal shape. Alternatively, the first recessed area 224 can have any cross-section that can be engaged to release pressure within the pressure chamber 214 such as square, rectangular, diagonal, latitudinal, circular, any polygonal shape, or a combination thereof. Further included along the inner wall 222 of the pressure chamber 214 is at least one second recessed area 228 configured to release pressure within the pressure chamber 214 and within the lumen 210 of the cannula 202. "At least one" second recessed area 228 as used herein includes one or more recessed area that extends along the inner wall 222 the distal end 220 of the pressure chamber 214. The second recessed area 228 is illustrated as having a longitudinal shape. Alternatively, the second recessed area 228 can have any cross-section that can be engaged to release pressure within the pressure chamber 214 such as square, rectangular, diagonal, latitudinal, circular, any polygonal shape, or a combination thereof.

The pressure chamber 214 includes a pressure generator 230 for generating a pressure in the pressure chamber 214 and altering a pressure in the lumen 210 of the cannula 202. In an embodiment and as shown in FIG. 2, the pressure generating device 230 may be a piston 232 disposed within the chamber 214. The piston 232 is dimensioned to engage the inner wall 222 of the pressure chamber 214. Typically, the piston 232 may be of any configuration to engage the inner wall 222 of the pressure chamber 214 in a substantially airtight fit. In an example, the piston 232 may be cylindrical in shape and have an outside diameter. Further, the inner wall 222 of the pressure chamber 214 may be cylindrical in shape wherein the outside diameter of the piston 232 is more than the diameter of the inner wall 222 to form a substantially airtight fit. "Substantially airtight fit" as used herein refers to a frictional fit of the inner wall 222 and the piston 232 to prevent any air from leaving the pressure chamber 214 through the distal end 220 of the pressure chamber 214. In an embodiment, the piston 232 and pressure chamber 214 may be of any suitable configuration to provide a substantially airtight fit.

As seen in FIG. 2, the piston 232 can include a body 234 having a proximal end 236 and a distal end 238. The proximal end 236 of the piston 232 can include a piston seal 240. The piston seal 240 may be configured to provide the substantially airtight fit between the inner wall 222 and the piston 232. The distal end 238 of the piston 232 can include a stem 242. The stem 242 is configured to move the piston 232 within the pressure chamber 214. The stem 242 may be incorporated into, or integrally formed with the distal end 238 of the piston 232. In an exemplary embodiment, as the piston 232 is depressed, the piston 232 moves toward the proximal end 218 of the pressure chamber 214. The stem 242 can have any cross-section that can be engaged for movement such as threaded, rectangular, any polygonal shape, or a combination thereof.

In a particular embodiment, the stem 242 is depressed and the piston 232 advances into the pressure chamber 214. In particular, depressing the piston 232 toward the proximal end 218 of the pressure chamber 214 but distal to the first recessed area 224 generates a positive pressure within the pressure chamber 214 and the lumen 210 of the cannula 202, relative to an atmospheric pressure. Further depressing the piston 232 to engage the first recessed area 224 releases the positive pressure within the pressure chamber 214 and the lumen 210 of the cannula 202. In an embodiment, the positive pressure is normalized to atmospheric pressure. In a further embodiment, advancing the piston 232 toward to distal end 220 of the pressure chamber 214 but proximal to the second recessed area 228 generates a negative pressure within the pressure chamber 214 and the lumen 210 of the cannula 202, relative to an atmospheric pressure. Further advancing the piston 232 to engage the second recessed area 228 releases the negative pressure within the pressure chamber 214 and the lumen 210 of the cannula 202. In an embodiment, the negative pressure is normalized to atmospheric pressure.

In a further embodiment, generating a negative pressure within the pressure chamber 214 provides pressure capable of removing a tissue sample from a biopsy cavity. Hence, the negative pressure provides a suction of the tissue sample from the biopsy cavity. The second recessed area 228 releases the negative pressure to prevent an excess build-up of pressure. Generating a positive pressure within the pressure chamber 214 provides pressure capable of removing the tissue sample from the biopsy device 200. The first recessed area 224 releases the positive pressure to prevent an excess build-up of pressure, resulting in a safe sample ejection.

As seen in FIG. 2, the proximal end 206 of the cannula 202 can include an orifice 212. The orifice 212 is located on a circumferential surface of the cannula 202. The orifice 212 on the circumferential surface of the cannula 202 forms the opening for access of a tissue sample in a tissue chamber 244 into the lumen 210 at the proximal end 206 of the cannula 202. In an embodiment, the orifice 212 may further include a cutting sheath 246 slidably disposed on the cannula 202. The cutting sheath 246 may be retracted toward the distal end 208 of the cannula 202 to expose the orifice 212 prior to removing a tissue sample from a biopsy cavity. When the proximal end 206 of the biopsy device 200 is placed in a biopsy cavity in a position to remove a tissue sample, the cutting sheath 246 may be advanced toward the proximal end 206 of the cannula 202 to reliably cut through a tissue sample and maintain the tissue sample within the tissue chamber 244 until sample ejection is desired.

In an embodiment, the cannula 202 may include a fluid receptacle 248. In a particular embodiment, the fluid receptacle 248 is located between the tissue chamber 244 and the pressure chamber 214. The fluid receptacle 248 may be of any suitable configuration to absorb any excess fluid that is received within the tissue chamber 244 during tissue sample removal. The fluid receptacle 248 traps the fluid so the fluids are contained within the fluid receptacle 248. In an embodiment, the fluid receptacle 248 is configured to absorb any blood or tissue as well as allow air to pass through the fluid receptacle 248. In an embodiment, the fluid receptacle 248 may be an absorbent material capable of absorbing fluid. An exemplary absorbent material is fabric such as cotton, cellulose, and polyvinyl alcohol (PVA).

Description of a Method of Extracting a Sample from a Biopsy Device

An exemplary, non-limiting embodiment of a method of controlling a pressure in a biopsy device is provide. In a first step, a biopsy device is provided. Subsequently, a cannula is inserted into a patient's body. At the distal end of the cannula is a pressure chamber having a body. The body of the chamber has a distal end and a proximal end. At least one first recessed area extends along an inner wall of the body, proximate the proximal end of the body of the chamber. The first recessed area is configured to release pressure within the chamber. At least one second recessed area extends along the inner wall of the body, proximate the distal end of the body of the chamber. The second recessed area is configured to release pressure within the chamber.

In a next step, a negative pressure environment, relative to an atmospheric pressure, is generated within the chamber. In an embodiment, the negative pressure is generated by advancing a piston toward the distal end of the chamber. The piston is configured to engage the inner wall of the chamber. In another step, a tissue sample is removed from the patient's body into a proximal inlet of the chamber. The tissue sample is removed as a result of the negative pressure environment generated within the chamber. Any fluid flow generated from the tissue sample removal may be absorbed by a fluid receptacle located at the proximal end of the chamber. Typically, the fluid receptacle may be any absorbent material capable of absorbing fluid. In a next step, the negative pressure environment may be released by engaging the second recessed area of the chamber. In an embodiment, the negative pressure may be released to atmospheric pressure. Subsequently, the biopsy device is removed from the patient's body.

In another step, a positive pressure environment, relative to an atmospheric pressure, is generated by advancing the piston toward the proximal end of the chamber. The positive pressure is released by engaging the first recessed area of the chamber. In an embodiment, the positive pressure is normalized to an atmospheric pressure when the first recessed area is engaged. Once the positive pressure is released, the tissue sample may be removed from the biopsy device. Subsequently, the method can end.

CONCLUSION

With the configuration of the structure described above, the biopsy device provides a device that allows for the safe removal of a tissue sample during a biopsy procedure. Further, the biopsy device is a system that does not necessitate the use of additional valves or automated means attached to the biopsy device to release any pressure build-up within the device that results in inadequate sample removal from a patient. As such, taking biopsy tissue samples using the biopsy device described herein is safe and user friendly.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A biopsy device comprising:
 a pressure chamber having a body having a distal end, a proximal end, and an inner wall, wherein the proximal end includes an inlet;
 at least one first recessed area extending along the inner wall of the body, proximate the proximal end of the body of the pressure chamber, wherein the first recessed area is configured to release pressure within the pressure chamber;
 at least one second recessed area extending along the inner wall of the body, proximate the distal end of the body of the pressure chamber, wherein the second recessed area is configured to release pressure within the pressure chamber;
 a piston configured to engage the inner wall of the pressure chamber;
 a cannula coupled to the pressure chamber for taking a tissue sample from a patient, the cannula defining a tissue chamber; and
 a fluid receptacle interposed between the tissue chamber and the pressure chamber, the fluid receptacle having an absorbent material to absorb a fluid,
 wherein the at least one first recessed area proximate the proximal end of the pressure chamber is configured to release a positive pressure within the pressure chamber.

2. A biopsy device comprising:
 a pressure chamber having a body having a distal end, a proximal end, and an inner wall, wherein the proximal end includes an inlet;
 at least one first recessed area extending along the inner wall of the body, proximate the proximal end of the body of the pressure chamber, wherein the first recessed area is configured to release pressure within the pressure chamber;
 at least one second recessed area extending along the inner wall of the body, proximate the distal end of the body of the pressure chamber, wherein the second recessed area is configured to release pressure within the pressure chamber;
 a piston configured to engage the inner wall of the pressure chamber;
 a cannula coupled to the pressure chamber for taking a tissue sample from a patient, the cannula defining a tissue chamber; and
 a fluid receptacle interposed between the tissue chamber and the pressure chamber, the fluid receptacle having an absorbent material to absorb a fluid,
 wherein as the piston is advanced toward the proximal end of the pressure chamber but distal to the at least one first recessed area, a positive pressure is created relative to an atmospheric pressure, and as the piston engages the at least one first recessed area, the positive pressure is released through the at least one first recessed area.

3. A biopsy device for tissue sample removal from a patient, comprising:
 a pressure chamber including a body having a distal end, a proximal end, and an inner wall, wherein the proximal end includes an inlet;
 a first recessed area extending along the inner wall of the body, wherein the first recessed area is configured to release positive pressure at a first location within the pressure chamber;
 a second recessed area extending along the inner wall of the body, wherein the second recessed area is configured to release negative pressure at a second location within the pressure chamber, the second location being spaced apart from the first location;
 a piston configured to engage the inner wall of the pressure chamber, and configured for movement over the first recessed area to release the positive pressure and configured for movement over the second recessed area to release the negative pressure;
 a cannula coupled to the inlet of the pressure chamber, the cannula having a tissue chamber configured to receive a tissue sample during tissue sample removal; and a fluid receptacle located between the tissue chamber and the pressure chamber, the fluid receptacle having an absorbent material to absorb a body fluid received in the tissue chamber during tissue sample removal.

4. The device of claim 3, wherein the cannula includes a first cannula portion and a second cannula portion, the first cannula portion being connected to the inlet of the pressure chamber, and the second cannula portion including the tissue chamber, wherein the fluid receptacle is interposed between the first cannula portion and the second cannula portion.

5. The device of claim 3, wherein the cannula includes a first cannula portion and a second cannula portion, the first cannula portion being connected to the inlet of the pressure chamber, and the second cannula portion including the tissue chamber, and wherein the fluid receptacle has a first fluid port and a second fluid port, the first fluid port being connected to the first cannula portion and the second fluid port being connected to the second cannula portion.

6. The device of claim 5, wherein the absorbent material is interposed between the first fluid port and the second fluid port of the fluid receptacle.

7. The device of claim 3, wherein the absorbent material is a fabric made from one of cotton, cellulose, or polyvinyl alcohol.

8. The device of claim 3, wherein the absorbent material is a polyvinyl alcohol fabric.

9. The device of claim 3, wherein the first recessed area proximate the proximal end of the pressure chamber is configured to release a positive pressure within the pressure chamber.

10. The device of claim 3, wherein the second recessed area proximate the distal end of the pressure chamber is configured to release negative pressure within the pressure chamber.

11. The device of claim 3, wherein as the piston is advanced toward the proximal end of the pressure chamber but distal to the first recessed area, a positive pressure is created relative to an atmospheric pressure, and as the piston engages the first recessed area, the positive pressure is released through the first recessed area.

12. The device of claim 3, wherein as the piston is advanced toward the distal end of the pressure chamber but proximal to the second recessed area, a negative pressure is created relative to an atmospheric pressure, and as the piston engages the second recessed area, the negative pressure is released through the second recessed area.

* * * * *